(12) United States Patent
Gokanakonda et al.

(10) Patent No.: US 11,238,518 B2
(45) Date of Patent: Feb. 1, 2022

(54) CUSTOMIZED PREDICTIVE FINANCIAL ADVISORY FOR A CUSTOMER

(71) Applicant: Wells Fargo Bank, N.A., San Francisco, CA (US)

(72) Inventors: Ravi Kumar Gokanakonda, Guntur (IN); Rameshchandra Bhaskar Ketharaju, Hyderabad (IN); Aravind Sastry Nudurupati, Hyderabad (IN); Venkata Rajesh Babu Evani, Hyderabad (IN)

(73) Assignee: Wells Fargo Bank, N.A., San Francisco, CA (US)

( * ) Notice: Subject to any disclaimer, the term of this patent is extended or adjusted under 35 U.S.C. 154(b) by 478 days.

(21) Appl. No.: 15/842,238

(22) Filed: Dec. 14, 2017

(65) Prior Publication Data

US 2019/0188769 A1 Jun. 20, 2019

(51) Int. Cl.
| | | |
|---|---|---|
| *G10L 13/10* | (2013.01) | |
| *G06Q 40/02* | (2012.01) | |
| *G02B 30/00* | (2020.01) | |
| *G06T 15/00* | (2011.01) | |
| *G06Q 30/06* | (2012.01) | |
| *G06Q 30/02* | (2012.01) | |
| *A61B 5/16* | (2006.01) | |
| *A61B 5/00* | (2006.01) | |

(52) U.S. Cl.
CPC ....... *G06Q 30/0631* (2013.01); *A61B 5/0022* (2013.01); *A61B 5/165* (2013.01); *G02B 30/00* (2020.01); *G06Q 30/0202* (2013.01); *G06Q 40/02* (2013.01); *G10L 13/10* (2013.01); *G06T 15/00* (2013.01)

(58) Field of Classification Search
None
See application file for complete search history.

(56) References Cited

U.S. PATENT DOCUMENTS

| | | | |
|---|---|---|---|
| 7,945,512 B2 | 5/2011 | Scipioni et al. | |
| 7,966,249 B1 * | 6/2011 | Dawson | G06Q 40/00 |
| | | | 705/37 |
| 8,407,137 B2 | 3/2013 | Thomas | |
| 8,478,691 B2 | 7/2013 | Solomon et al. | |
| 8,583,769 B1 | 11/2013 | Peters et al. | |
| 8,606,610 B2 * | 12/2013 | Black | G06F 30/20 |
| | | | 705/7.12 |
| 9,011,155 B2 | 4/2015 | Skelton et al. | |
| 9,399,111 B1 | 7/2016 | Hanina | |

(Continued)

OTHER PUBLICATIONS

Burke et al., Trust and Financial Advice, Rand Labor & Population (Year: 2015).*

(Continued)

*Primary Examiner* — David P Sharvin
*Assistant Examiner* — Brock E Turk
(74) *Attorney, Agent, or Firm* — Womble Bond Dickinson (US) LLP

(57) ABSTRACT

A system, method and computer program product provide for intervening in a financial transaction to discourage a bad decision by a customer. An execution decision by a customer is analyzed. A cautionary rule that is violated by the execution decision is identified. A suggestion in a personally persuasive persona presented on at least one user interface device to the customer.

16 Claims, 7 Drawing Sheets

(56) References Cited

U.S. PATENT DOCUMENTS

| | | | |
|---|---|---|---|
| 2006/0195787 A1* | 8/2006 | Topiwala | H04N 21/41407 |
| | | | 715/700 |
| 2006/0200432 A1* | 9/2006 | Flinn | G06N 7/02 |
| | | | 706/12 |
| 2010/0250421 A1 | 9/2010 | Ariff et al. | |
| 2010/0268629 A1 | 10/2010 | Ross et al. | |
| 2011/0246387 A1 | 10/2011 | Ross et al. | |
| 2012/0130887 A1 | 5/2012 | Meckling | |
| 2012/0215597 A1* | 8/2012 | Ross | G06Q 30/0201 |
| | | | 705/14.1 |
| 2012/0296768 A1 | 11/2012 | Fremont-Smith et al. | |
| 2012/0303519 A1 | 11/2012 | Burke | |
| 2013/0050260 A1* | 2/2013 | Reitan | G09G 5/377 |
| | | | 345/633 |
| 2013/0191194 A1 | 7/2013 | Shreibati et al. | |
| 2013/0198064 A1 | 8/2013 | Sobut | |
| 2013/0311528 A1 | 11/2013 | Liebermann | |
| 2014/0114735 A1 | 4/2014 | Isaacson et al. | |
| 2014/0136365 A1 | 5/2014 | Nista | |
| 2014/0164086 A1 | 6/2014 | Coffman et al. | |
| 2014/0365355 A1* | 12/2014 | Shvarts | G06Q 40/02 |
| | | | 705/38 |
| 2015/0106236 A1 | 4/2015 | Morris et al. | |
| 2016/0034932 A1* | 2/2016 | Sion | G06Q 40/00 |
| | | | 705/14.1 |
| 2016/0321935 A1* | 11/2016 | Mohler | G09B 5/08 |
| 2017/0046496 A1* | 2/2017 | Johnstone | G06F 19/00 |
| 2018/0176727 A1* | 6/2018 | Williams | A61B 5/747 |
| 2018/0336048 A1* | 11/2018 | Zarlengo | G06F 9/453 |
| 2019/0087846 A1* | 3/2019 | Liu | G06Q 30/0239 |

OTHER PUBLICATIONS

C Lopez, Juan, Sinisa Babcic, and Andres De La Ossa. "Advice goes virtual: how new digital investment services are changing the wealth management landscape." Journal of Financial Perspectives 3.3, 2015 (Year: 2015).*

Ally Financial. "Ally Financial Launches New Splurge Alert App in Beta, Inviting Consumers to Come Clean on Overspending Habits with Help of Friends", PR Newswire, Apr. 18, 2016, retrieved from the internet at: http://www.prnewswire.com/news-releases/ally-financial-launches-new-splurge-alert-app-in-beta-inviting-consumers-to-come-clean-on-overspending-habits-with-help-of-friends-300252894.html.

Tom Cheredar. "Urge app helps you keep impulse spending in check (exclusive)", Venturebeat, Feb. 6, 2012, retrieved from the internet at: https://venturebeat.com/2012/02/06/urge-iphone-app/.

* cited by examiner ial transaction, the customer had to interact exten-
CUSTOMIZED PREDICTIVE FINANCIAL ADVISORY FOR A CUSTOMER

BACKGROUND

The present application relates to systems and methods for analyzing financial transaction opportunities and interacting with a user.

Financial institutions facilitate financially-related transactions for customers such as purchases, sales, investments, and divestitures. Before the advent of automation of many of the tasks associated with contemplating and executing a financsively with at least one employee of the financial institution before any action was taken. The financial institution often sought to have the employee gain an understanding of the customer and gain the trust of the customer in order to have an ongoing, mutually-beneficial business relationship. The employee could gauge many factors associated with the transaction, such as: (i) the objective advisability of the transaction; (ii) the subjective advisability of the transaction for the particular customer; (iii) the mental capacity of customer in general or at the particular moment in time; and (iv) the emotional state of the customer. In addition, generally a certain length of time elapsed during the process, affording the customer time to reconsider any decisions made.

A knowledgeable and trusted employee of the financial institution is the ideal. Financial sectors may hire a counsellor for intervening in customer decisions and advising customers by providing pros and cons of a situation. However, hiring counsellors may have a risk factor such as the counsellors may be biased, not knowledgeable or experienced to provide correct suggestions. The counsellor may not know the customer or his behavior and the like.

Recent technological advancements have automated many of the analytical tools and transactions channels. There exist automated systems that receive user query and provide a predefined response to the user query. Customers are empowered to self-educate themselves on financial opportunities, if they choose, and to cause a financial transaction to execute. The cost and time required to effect such an outcome becomes increasingly small. Preferring the anonymity, many customers are not prone to seek out guidance from human experts even when such advice is needed. Emotions or mood of a person have a huge impact on the decisions that he makes. Neutral or happy emotions lead to good decisions. Conversely, when the person is in a bad mood or an abnormal state of mind such as extreme anger, intoxicated and the like, his decisions may be wrong and impulsive. Also, the expectations and anxiety in such abnormal state of mind would be different and high. These wrong decisions may have a catastrophic impact in the near future, especially, when the decisions are related to financial aspects. The person might be badly affected.

BRIEF DESCRIPTION

This brief description is provided to introduce a selection of concepts in a simplified form that are described below in the detailed description. This brief description is not intended to be an extensive overview of the claimed subject matter, identify key factors or essential features of the claimed subject matter, nor is it intended to be used to limit the scope of the claimed subject matter.

The existing techniques do not consider emotions, sentiments and mood of the customer in providing suggestions to the customer. Hence, there is need for an automated virtual technique that comprises intelligence to intervene into the decisions of the customer and provides suggestions. By analyzing the emotion, mood and sentimental of the customer, a persuasively conveyed suggestion can dissuade the customer from making wrong decisions.

In one or more embodiments, the present disclosure provides a method of intervening in a financial transaction to discourage a bad decision by a customer. In one or more embodiments, the method includes analyzing an execution decision by a customer for a financial transaction. The method includes identifying a cautionary rule that is violated by the execution decision. The method includes presenting on at least one user interface device to the customer a suggestion in a personally persuasive persona.

In one or more embodiments, the present disclosure provides a system including an input engine that monitors at least one user interface device of a customer. The system includes an analysis engine that: (i) analyzes an execution decision by the customer made on the user interface device for a financial transaction; and (ii) identifies a cautionary rule that is violated by the execution decision. The system includes a virtualization engine that presents on at least one user interface device to the customer a suggestion in a personally persuasive persona.

In one or more embodiments, the present disclosure provides a computer-readable storage medium includes computer-executable instructions. When executed via a processing unit on a computer, the computer-readable storage medium performs acts including: (i) analyzing an execution decision by a customer for a financial transaction; (ii) identifying a cautionary rule that is violated by the execution decision; and (iii) presenting on at least one user interface device to the customer a suggestion in a personally persuasive persona.

The following description and annexed drawings set forth certain illustrative aspects and implementations. These are indicative of but a few of the various ways in which one or more aspects may be employed. Other aspects, advantages, or novel features of the disclosure will become apparent from the following detailed description when considered in conjunction with the annexed drawings.

BRIEF DESCRIPTION OF THE DRAWINGS

Aspects of the disclosure are understood from the following detailed description when read with the accompanying drawings. Elements, structures, etc. of the drawings may not necessarily be drawn to scale. Accordingly, the dimensions of the same may be arbitrarily increased or reduced for clarity of discussion, for example.

DETAILED DESCRIPTION

Figure 1:
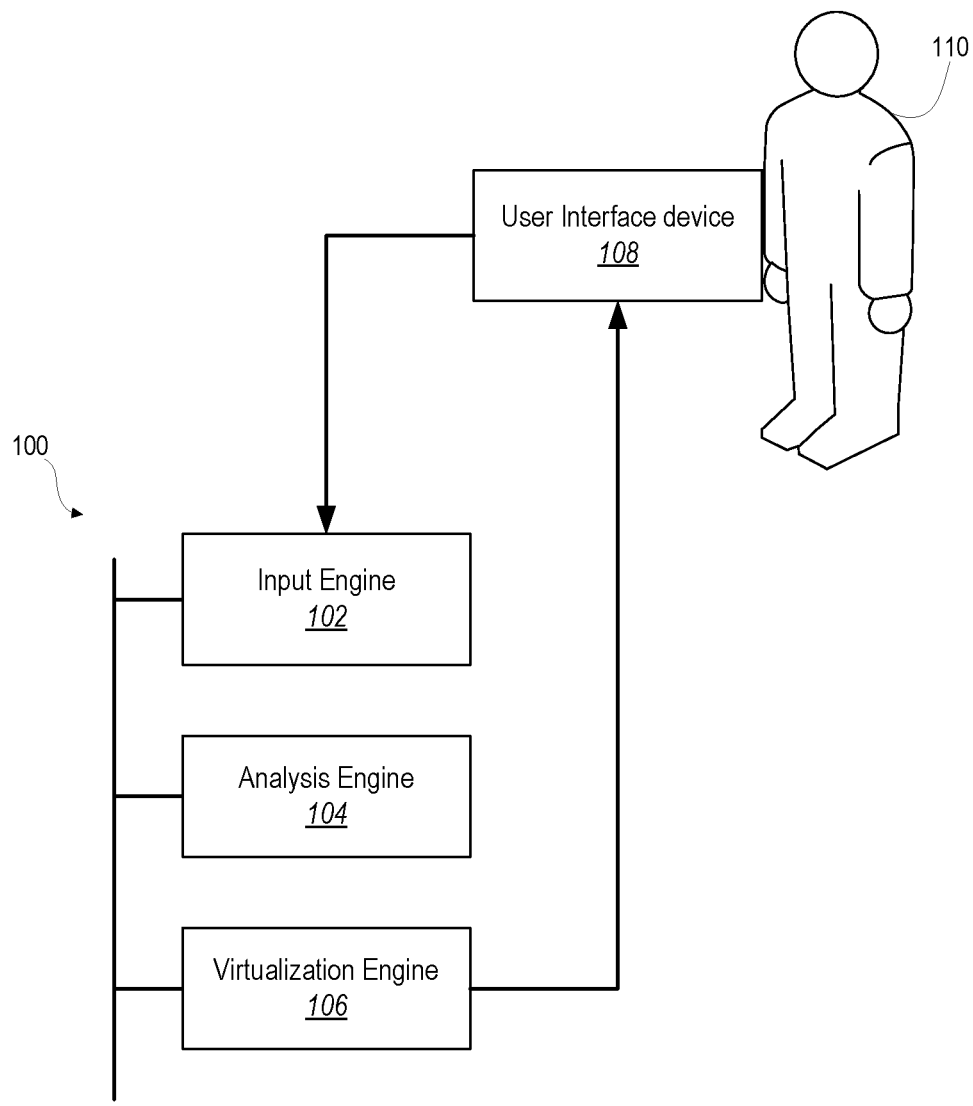
FIG. 1 illustrates a block diagram of a system for avoiding or mitigating bad decision making by a customer, according to one or more embodiments.

In one or more embodiments, the present disclosure provides an intervention or "guardian angel" system to stop wrong or impulsive financial decisions taken by a customer due to an abnormal state of mind. The intervention/guardian angel system determines whether the decision taken by the customer is a wrong or impulsive decision based on various factors such as: (i) background factors that provide information on personality of the customer; (ii) social factors that provide information on peers and network of the customer; (iii) short term risk factors of the customer; and (iv) emotions, sentiments and mood of the customer. To prevent the customer from implementing the wrong or impulsive decision taken during an abnormal state of mind, the intervention/guardian angel system would create a virtual environment comprising holograms of the people in customer's network.

In an embodiment, the holograms would be trained to emulate voice, actions, expressions, personality traits and emotions of the person whom the hologram represents. Different suggestions related to the wrong/impulsive decision taken by the customer would be highlighted to the customer via the virtualized environment with holograms. The suggestions would be mapped with personality of the people in the customer's network based on emotional relationship the customer shares with a person in his network and displayed to the customer accordingly. As an example, if the customer impulsively decides to buy an expensive bike, the intervention/guardian system would analyze his financial health and infer that this is a wrong decision. Based on the impact of the wrong/impulsive decision made by the customer, the intervention/guardian system would appropriately choose the holograms that have the capacity to stop the customer's decision and display the suggestions.

According to aspects of the present innovation, the intervention/guardian system provides a number of features that include: (i) Detecting the situations when the user requires assistance or suggestions based on the sensor data and real-time customer data; (ii) Emulating behaviors of various users with respect to their voice, appearance, gestures, personality, thought process, emotional intelligence, body language using flavors of data intelligence or cognitive computing, neural technology, intelligent data or cognitive data; (iii) Automatically selecting apt hologram having utmost impact on the customer based on the situation which the customer is facing and the input factors; (iv) Automatically selecting apt mode and interface for projecting the suggestions through the selected holograms based on urgency of the situation, type of suggestions to be provided, number of suggestions to be provided and the like; (v) Creating a virtualized environment which gives an illusion that the people whom the customer would require suggestions from in a certain situation, are actually present and are actively participating, like in real world; and (vi) Emulating behaviors of various users in the virtualized environment with respect to their voice, appearance, gestures, personality, thought process, emotional intelligence, body language using flavors of data intelligence or cognitive computing, neural technology, intelligent data or cognitive data.

By automatically intervening in a persuasive manner, the present innovation prevents financial loss to the customer due to wrong or impulsive decisions. System builds a trust factor for the customer. For example, the customer would trust the suggestions of the intervention/guardian system since the intervention/guardian system provides unbiased suggestions. Holograms emotionally trigger the customer and provides a better chance of convincing the customer to stop his decision. Real-time availability of a person in the form of a hologram emulates the person when the customer needs their opinion.

Embodiments or examples, illustrated in the drawings are disclosed below using specific language. It will nevertheless be understood that the embodiments or examples are not intended to be limiting. Any alterations and modifications in the disclosed embodiments, and any further applications of the principles disclosed in this document are contemplated as would normally occur to one of ordinary skill in the pertinent art.

The following terms are used throughout the disclosure, the definitions of which are provided herein to assist in understanding one or more aspects of the disclosure.

As used herein, the term "infer" or "inference" generally refer to the process of reasoning about or inferring states of a system, a component, an environment, a user from one or more observations captured via events or data, etc. Inference may be employed to identify a context or an action or may be employed to generate a probability distribution over states, for example. An inference may be probabilistic. For example, computation of a probability distribution over states of interest based on a consideration of data or events. Inference may also refer to techniques employed for composing higher-level events from a set of events or data. Such inference may result in the construction of new events or new actions from a set of observed events or stored event data, whether or not the events are correlated in close temporal proximity, and whether the events and data come from one or several event and data sources.

Turning to the Drawings, FIG. 1 illustrates a system 100 having an input engine 102, an analysis engine 104, and a virtualization engine 106 for avoiding or mitigating bad decision making by a customer. The input engine 102 monitors at least one user interface device 108 of a customer 110. The analysis engine 104 (i) analyzes an execution decision by the customer 110 made on the user interface device 108 for a financial transaction; and (ii) identifies a cautionary rule that is violated by the execution decision. The virtualization engine 106 presents on at least one user interface device 108 to the customer 110 a suggestion in a personally persuasive persona.

In one or more embodiments, the input engine 102: (i) monitors the user interface device 108 of the customer 110 during communication with one or more persons; and (ii) detects a response to the selected person of the one or more persons. The analysis engine 104 determines that the response is positive to a selected person of the one or more persons that indicates persuasive relationship with the customer 110. The virtualization engine 106 captures the persona of the selected person for communicating with the customer 110 via the user interface device 108.

In one or more embodiments, the analysis engine 104 determines the positive response to the selected person of the one or more persons that indicates persuasive relationship with the customer 110 by a selected one of: (i) associating a good decision occurring after a corresponding suggestion by the selected person to the customer 110; and (ii) detecting a positive emotional response comprising: (a) determining that the selected person is communicating with the customer 110; (b) detecting a physiological response by the customer 110 to the communication; and (c) determining that the physiological response correlates to a persuasive relationship.

In one or more embodiments, the analysis engine 104: (i) determines a positive response by the customer 110 to another person; (ii) characterizes the selected person as having persuasive relationship with the customer 110 in a first type of financial transaction; (iii) characterizes the other person as having persuasive relationship with the customer 110 in a second type of financial transaction; and (iv) determines that the financial transaction is the first type. The virtualization engine 106 presents the suggestion in the personally persuasive persona of the selected person in response to the analysis engine 104 determining that the financial transaction is the first type.

In one or more embodiments, the virtualization engine 106 captures the persona by: (i) rendering an image of the selected person into a three-dimensional holographic image; and (ii) setting voice qualities of text-to-voice playback to mimic speech by the selected person.

In one or more embodiments, the input engine 102 monitors at least one of: (i) a bio sensor proximate to the customer 110; and (ii) a communication channel of the user interface device 108 utilized by the customer 110 to obtain real-time data about the customer 110. The analysis engine 104 determines a degree to which the customer is at least one of: (i) mentally incapacitated; and (ii) emotionally overwrought based at least in part on the real-time data. The analysis engine 104 identifies that the cautionary rule is violated by the execution decision by determining that the degree satisfies a criterion of the cautionary rule for inability to make a good decision.

In one or more embodiments, the analysis engine 104 identifies that the cautionary rule is violated by the execution decision by identifying that the execution decision by the customer 110 is made at an inappropriate time comprising: (i) identifying an event that has occurred for the customer 110 within a time interval; and (ii) associating the event and the time interval with the cautionary rule.

In one or more embodiments, the analysis engine 104 identifies that the cautionary rule is violated by the execution decision by identifying that the execution decision by the customer is objectively a bad decision by: (i) associating the financial transaction with a market prediction maintained in a financial sector system; (ii) determining that the execution decision is opposite to a recommendation based on the market prediction.

In one or more embodiments, the analysis engine 104 identifies that the cautionary rule is violated by the execution decision by identifying that the execution decision by the customer 110 is subjectively a bad decision comprising: (i) accessing personal financial information associated with the customer 110; and (ii) determining that the execution decision is opposite to a recommendation derived from the cautionary rule based on the personal financial information.

In one or more embodiments, the analysis engine 104: (i) identifies a prioritized list of recommended financial transactions appropriate for the customer 110; and (ii) identifies the cautionary rule that is violated by the execution decision by determining based on the personal financial information that execution decision prevents execution of a recommended financial transaction that is higher priority.

Figure 2:
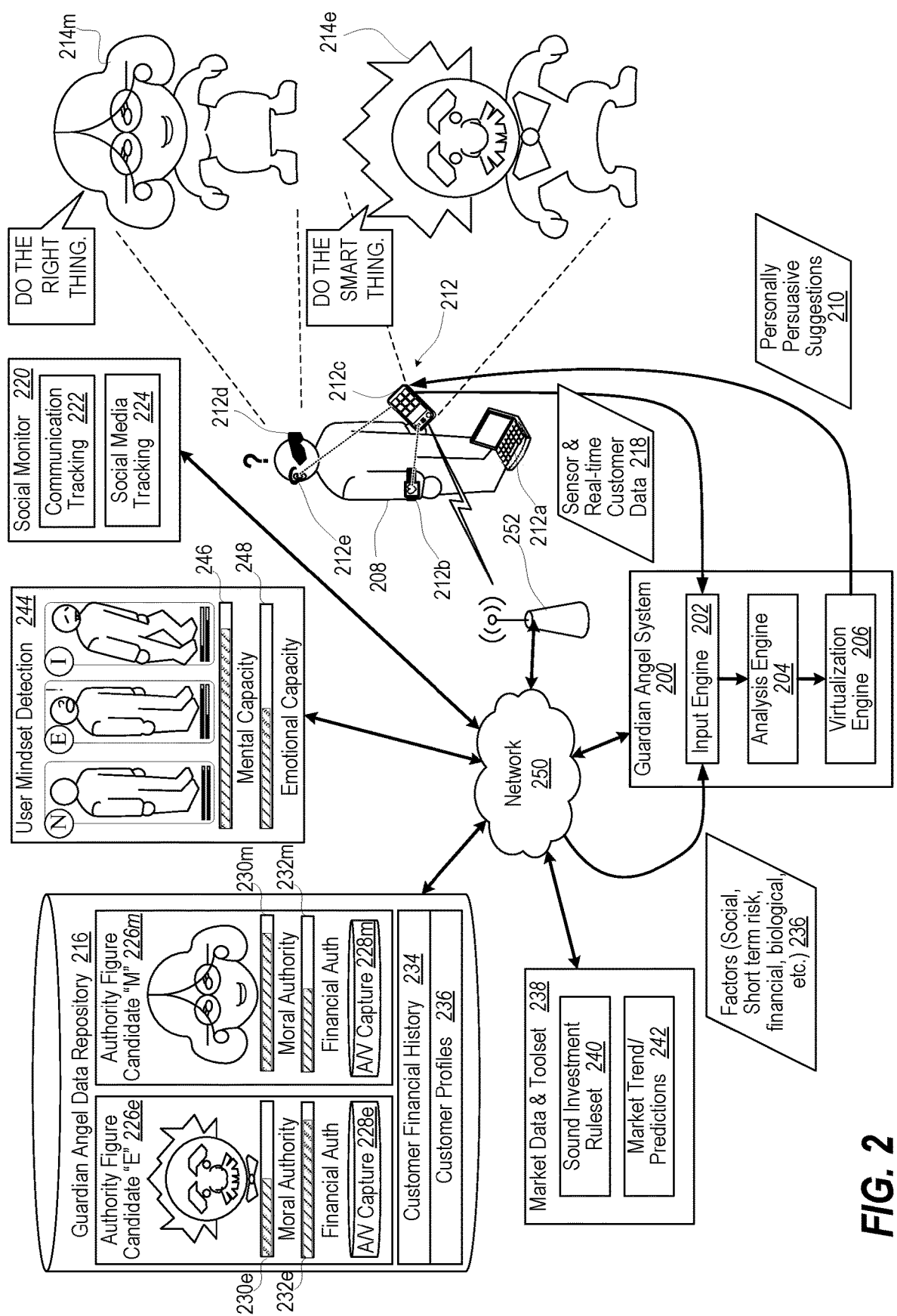
FIG. 2 illustrates a block diagram of a guardian angel system that prevents, or at least persuasively discourages, a customer from making wrong decisions by presenting suggestions, according to one or more embodiments.

In one or more embodiments, FIG. 2 illustrates a guardian angel system 200 having input, analysis and virtualization engines 202, 204, 206 that prevent, or at least persuasively discourage, a customer 208 from making wrong decisions by presenting suggestions 210. In an exemplary embodiment, at least one user interface device 212 is capable of presenting these suggestions in a selected persona 214*m* that is known and trusted by the customer 208. For example, the customer 208 can utilize a laptop computer 212*a*, a smart watch 212*b*, a smart phone 212*c*, virtual or augmented reality goggles 212*d*, and an earpiece 212*e*. Any of the at least one user interface devices 212 can also provide sensor and real-time customer data 218 to the guardian angel system 200.

In one or more embodiments, the selected persona 214*m* can be deemed particularly persuasive to the type of decision under consideration as compared to another persona 214*e*. The guardian angel system 200 can utilize a social monitor system 220 that has a communication tracking component 222 and a social media tracking component 224 to identify individuals who communicate and interact with the customer 208. Based on how the customer 208 reacts to such communications, a profile for each authority figure candidate, such as candidate "E" profile 226*e* and candidate "M" profile 226*m* can correspond to personas 214*e*, 214*m*. The personas 214*e*, 214*m* resemble the respective individuals based on audio/video (A/V) capture 228*e*, 228*m*. Sensed emotional reactions or the type of decisions made by the customer 208 in response to actual communications with particular individuals can be used to infer how personally persuasive each individual is to the customer 208. For example, a moral authority gauge 230*e* for candidate "E" profile 226*e* can be lower than a moral authority gauge 230*m* for candidate "M" profile 226*m*. A financial authority gauge 232*e* for candidate "E" profile 226*e* can be higher than a financial authority gauge 232*m* for candidate "M" profile 226*m*. The data repository 216 can also contain a financial history 234 for the customer 208. The data repository 216 can also contain a customer profile 236 for the customer 208, such as voluntarily divulged information and data gleaned from public sources.

The guardian angel system 200 utilizes one or more input factors 236 received by the input engine 202 to decide whether a decision taken by the customer 208 is a good or a bad decision. For example, input factors 236 can include social factors, short-term risk, financial factors, biological factors, etc. The guardian angel system 200 can utilize market data and toolsets 238, such as including sound investment rule set 240 and market trend/prediction data 242. The guardian angel system 200 can also utilize a user mindset detection system 244, such as characterizing a normal condition "N", an emotionally overwrought state "E", and an intoxicated state "I" based on relative measures of mental capacity 246 and emotional capacity 248.

For clarity, various functions and affiliated systems for the guardian angel system 200 are depicted as distributed over a network 250. The user interface device(s) 212 is coupled to the network 250 over a node 252. However, all of the functionality can be orchestrated by one device or a smaller combination of devices. If distributed, the network 250 can include portions that are hardwired, coupled over a wireless area network, wireless wide area network, personal access network, etc.

The decision made by the customer 208 can be bad because: (i) the decision is objectively bad in general for all customers; (ii) the decision is subjectively bad for the particular situation of the specific customer 208 in question; or (iii) the way that the decision is made is wrong for being too rash or impulsive. Herein, the bad decisions are referred to then as either wrong or impulsive decision. What remain after the wrong and impulsive decisions are determined are then good decisions. The input engine 202 collects all the required input factors required for analysis in real-time and stores the input factors in a data repository 216.

In an embodiment, the input factors are broadly classified into background factors, social factors, short term risk factors, financial factors and external factors. The background factors may provide information on personality of the customer 208. The personality of the customer 208 may be inferred based on impulsiveness of the customer 208, age and location of the customer 208 and the like. For example, if the customer 208 is around 35 years old and is staying in a different location from his family, his main objective or intention would be to save money and purchase a house such that his family stays with him. Social factors include information on peers of the customer 208, peer pressure faced by the customer 208, network of the customer 208 and the like. The peer pressure may make the customer 208 believe that he has to match up to expectations of his peers and may make unnecessary expenditure though it is not in his budget. Network of the customer 208 may include family members, friends, and office networks.

The guardian angel system 200 may perform cash flow analysis such as debits, credits, income history of the customer 208 as well as the close family members in the network to exactly understand how social factors are affecting decisions of the customer 208. Short term risk factors may include some unusual behavior of the customer 208 in a short span of time. As an example, when the customer 208 is in an abnormal state of mind due to consumption of alcohol, he may impulsively decide to buy a very expensive car which does not support his financial health. Impaired travel patterns of the customer 208 could be tracked to prevent such impulsive decisions. As an example, the customer 208 may generally go home or to some restaurants after office hours but not to a car showroom. Therefore, this would become an impaired travel pattern. Financial factors may provide information on financial health of the customer 208, short term and long term goals of the customer 208 and the like. External factors would be the emotions, mood and sentiments of the customer 208, reaction of the customer 208 to certain situations such as stock market crash and the like. The analysis engine 204 retrieves the input factors from the data repository 216 to perform real-time analysis based on the real-time information stored in the data repository 216.

Further, the input engine 202 collects biological factors such as voice, images, text messages, body language, gestures and thought process of the customer 208 and the people in the close network of the customer 208 such as mother, father, siblings, friends and the like. The input engine 202 may extract voice based on phone calls, video chats, voice messages etc. of the customer 208, images from database of the customer 208, text messages from various message applications such as whatsapp, Messenger, Gtalk and the like, body language and gestures based on video calls, stored videos and the like. Some other factors such as emotional intelligence, awareness, knowledge, relationship status and the like are derived factors. The data repository 216 stores this type of information for future use.

The analysis engine 204 performs real-time analysis based on all the input factors to understand the customer 208. The real-time analysis allows the guardian angel system 200 to self-learn and to be intelligent enough to decide whether the decision made by the customer 208 is a wrong decision or not. Further, the analysis engine 204 analyses the biological factors to derive voice modulation, emotional intelligence, awareness, knowledge, relationship status and the like of the customer 208 and the people in the network of the customer 208. The analysis may be based on various next generation data concepts that comprise flavors of data intelligence or cognitive computing, neural technology, intelligent data or cognitive data, big data analysis techniques and the like.

Based on the analysis, the virtualization engine 206 creates a virtualized environment to intervene into the decisions of the customer 208. The virtualization environment may be an emulation of the people in the network of the customer 208 in the form of holograms.

As an example, consider a scenario where the customer 208 wants to invest his entire savings on buying an expensive car. The analysis engine 204 would analyze based on the input factors, emulating which person/a group of people in the network of the customer 208 would have a better impact on the mind of the customer 208. As an example, the guardian angel system 200 is intelligent enough to analyze that if the topic is related to property, the customer 208 would like to have his father's opinion, if the topic is related to technology, the customer 208 would like to have his friends opinion and the like. Consider the analysis engine 204 chose a group of friends of the customer 208 on a messaging platform such as "Whatsapp". The group of friends may include a best friend of the customer 208 who has most impact on the customer 208. The virtualization engine 206 creates a virtual environment that comprises emulated holograms of the group of friends of the customer 208. The virtualization engine 206 would pick the suggestions for the customer 208 and project the suggestions as a message from one of the friends in the group. In an embodiment, the suggestions are mapped to each friend on the group based on their personality traits. As an example, if one of the friend is impulsive, the hologram of this friend would suggest to the customer 208 "Hey good decision. Please go ahead. I'm waiting to drive your new car." On the other hand, if one of the friend is thoughtful and a close friend of the customer 208 who knows the behavior of the customer 208, the hologram of this friend would suggest to the customer 208 "May be it is not a good idea to spend your entire savings on an expensive car. Wait for a few more years or buy a basic car". Therefore, the guardian angel system 200 has the intelligence to map the suggestions to apt holograms. The virtualized environment would build a trust factor for the customer 208 due to the emulated appearance of apt people in the life of the customer 208 to provide suggestions at the correct time. The guardian angel system 200 would provide apt suggestions to the customer 208 based on the input factors. If the customer 208 chooses to ignore the suggestions and go ahead with his wrong decision, then it may be considered as an unforced error. Such unforced errors are stored for future use to determine behavior of the customer 208 in various situations.

Further, the guardian angel system 200 has the intelligence to select the apt mode/apt interface to project the suggestions to the customer 208. In an embodiment, the apt mode/apt interface may be a message application such as Whatsapp, messenger and the like, a phone call, a video call and the like. As an example, if the suggestion has to be given on an urgent/emergency basis, the guardian angel system 200 would select a video call as the mode to project the suggestions to the customer 208 and a hologram of the person who has the utmost impact on the customer 208 in such situations through whom the suggestion could be projected. Hologram of the person along with voice modulation, body language, gestures, appearance and the like would appear in the virtualized environment to provide suggestions to the customer 208. As an example, if many suggestions may be given to the customer 208 from which he can choose, the guardian angel system 200 would choose a group of his friends/family and project the suggestions by mapping each suggestion to personality of each person in the group. In another embodiment, the customer 208 can preconfigure what mode/interface and which person/group of people he would prefer in certain situations.

In an embodiment, the guardian angel system 200 would detect the necessity of suggestions for the customer 208 based on sensor data and real-time data associated with the customer 208. The guardian angel system 200 would continuously monitor phone calls, video calls, chat history, medical history, history of the nearest family members, reactions of the customer 208 in different situations, social network keywords used by the customer 208 and his network, check-ins, photos, videos and the like to obtain customer 208 data. Further, sensors could be configured in the mobile phones or other computing devices of the customer 208 that would detect the pressure applied by the user on the phone or sensors that would detect if the customer 208 is using abusive language after seeing a message or finishing a call. Based on each of the above mentioned actions of the customer 208, the guardian angel system 200 would be automatically triggered to create a virtualized environment, emulate behaviors of various people using holograms and project a suggestion to the customer 208. In another embodiment, the customer 208 himself can activate the guardian angel system 200 and seek suggestions.

Thus, the guardian angel system 200 continuously monitors sensor data and real-time customer data to detect a situation where the customer 208 may require assistance in choosing a right decision. Based on the situation, if the customer 208 has made a decision, the guardian angel system 200 analyzes the circumstances to determine if the decision is correct or a wrong decision based on various input factors. If the decision is wrong and the customer 208 needs to be assisted in decision making, the guardian angel system 200 selects apt holograms and apt mode to project suggestions to the customer 208 based on various input factors. Further, the guardian angel system 200 creates a virtualized environment comprising emulated versions of the people in network of the customer 208 in the form of holograms and projects the suggestions to the customer 208 through the holograms based on the selected mode of projecting the suggestions.

An example use case regards comparing an advertisement value. Based on augmented reality or Global Positioning System (GPS), the guardian angel system 200 can detect that the customer 208 is in a certain location/certain store. The guardian angel system 200 would predict the product that he may be wishing to buy based on real-time customer data. As an example, the product may be a toy that he would buy for his daughter. If price of the product is contradicting financial status of the customer, the guardian angel system 200 would analyze the customer's accumulated profile data to determine which hologram might impact the customer best. For example, the guardian angel system 200 selected hologram of the customer's daughter could project "Dad I need books for school. Please don't buy this toy now." The hologram of his daughter would invoke a guilt feeling in the customer and has the capability to stop the impulsive purchase.

Figure 3:
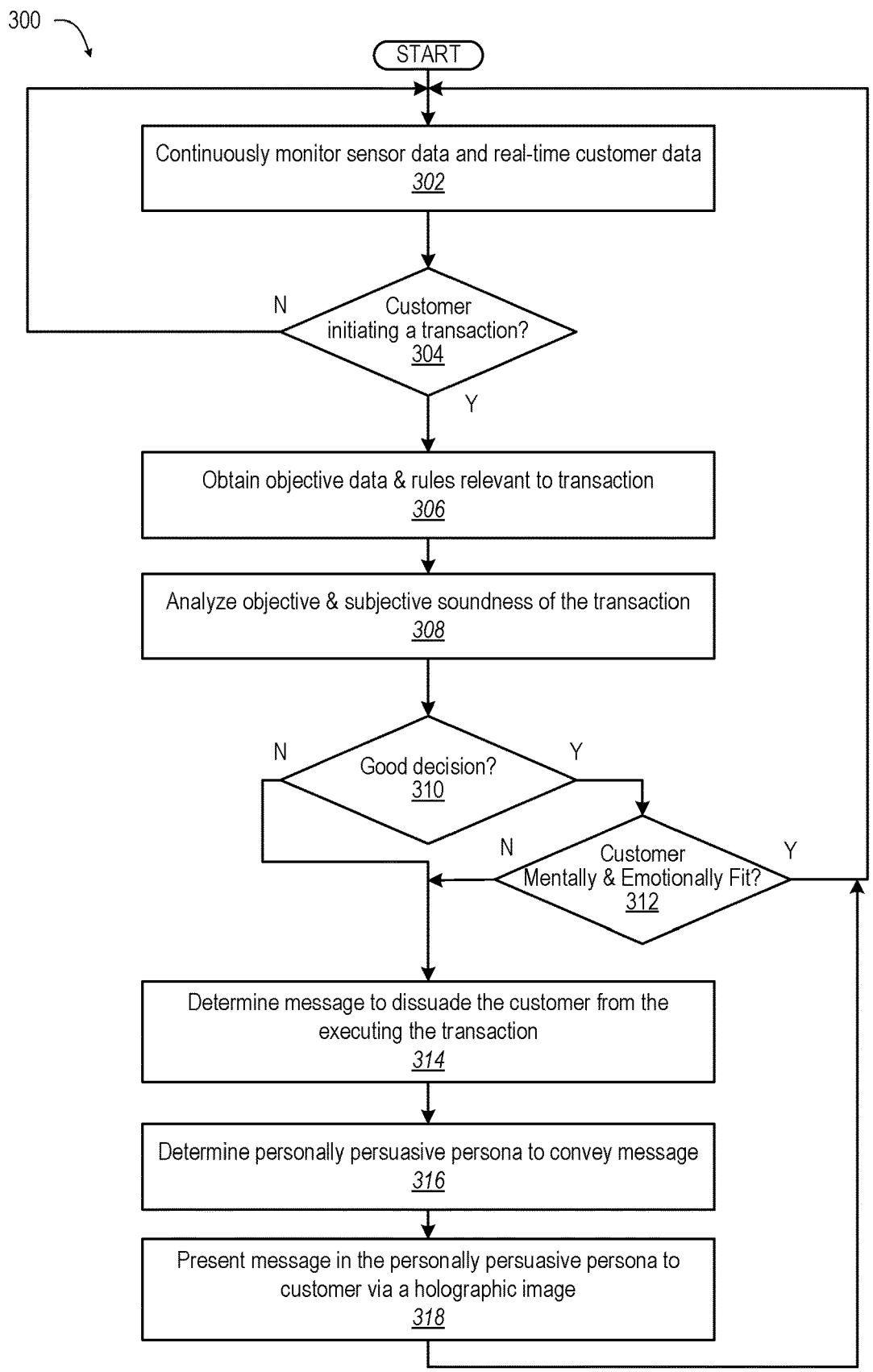
FIG. 3 illustrates a flow diagram of a method of intervening in a customer's bad decision with a persuasive holographic suggestion, according to one or more embodiments.

FIG. 3 illustrates a method 300 of intervening in a customer's bad decision with a persuasive holographic suggestion. Method 300 begins continuously monitoring sensor data and real-time customer data (block 302). A determination is made as to whether the customer is initiating a transaction (decision block 304). If not initiating a transaction, method 300 returns to block 302 to continue monitoring. In response to determining that a transaction is initiated, method 300 includes obtaining objective data and rules relevant to the transaction (block 306). Method 300 includes analyzing objective and subjective soundness of the transaction (block 308). A determination is made as to whether the transaction is objectively and subjectively good decision (decision block 310). In response to determining that the transaction is a good decision, a further determination is made as to whether the customer is mentally and emotionally fit to make a decision (decision block 312). In response to determining that the client is mentally and emotionally fit, method 300 returns to block 302 to continue monitoring for a situation that warrants intervention. In response to determining that the transaction is not a good decision in decision block 310 or in response to determining that the customer is not mentally and emotionally fit to make a decision in decision block 312, method 300 includes determining a message to dissuade the customer from executing the transaction (block 314). Method 300 includes determining a personally persuasive persona to convey the message (block 316). Method 300 incudes presenting the message in the personally persuasive persona to the customer via a holographic image (block 318). Then method 300 returns to block 302 to continue monitoring for a situation that warrants intervention.

Figure 4:
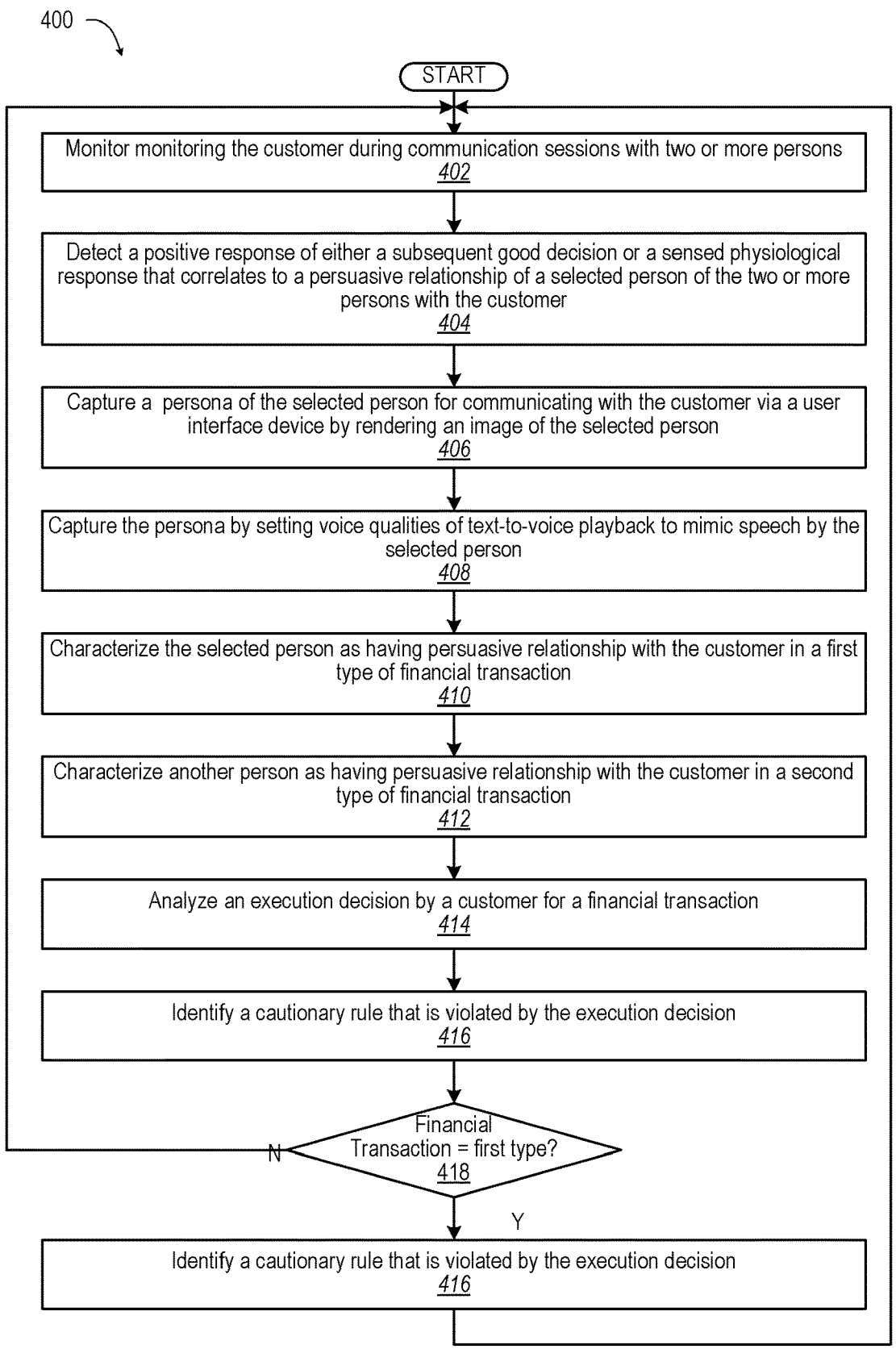
FIG. 4 illustrates a flow diagram of a method of intervening in a financial transaction to discourage a bad decision by a customer, according to one or more embodiments.

FIG. 4 illustrates a method 400 of intervening in a financial transaction to discourage a bad decision by a customer. In one or more embodiments, method 400 begins monitoring the customer during communication sessions with two or more persons (block 402). Method 400 includes detecting a positive response of either a subsequent good decision or a sensed physiological response that correlates to a persuasive relationship of a selected person of the two or more persons with the customer (block 404). Method 400 includes capturing a persona of the selected person for communicating with the customer via a user interface device by rendering an image of the selected person (block 406). For example, the rendered image can be a three-dimensional holographic image. Alternatively or in addition, method 406 includes setting voice qualities of text-to-voice playback to mimic speech by the selected person (block 408).

In an exemplary embodiment, method 400 includes characterizing the selected person as having persuasive relationship with the customer in a first type of financial transaction (block 410). Method 400 can include characterizing another person as having persuasive relationship with the customer in a second type of financial transaction (block 412).

Method 400 includes analyzing an execution decision by a customer for a financial transaction (block 414). Method 400 includes identifying a cautionary rule that is violated by the execution decision (block 416). A determination is made as to whether the financial transaction is of the first type (decision block 418). In response to determining that the financial transaction is of the first type, method 400 includes presenting on at least one user interface device to the customer a suggestion in a personally persuasive persona of the selected person (block 420). Then method 400 returns to block 402 to continue monitoring for opportunities to intervene in a bad decision by the customer. In response to determining that the financial transaction is not the first type in decision block 418, method 400 returns to block 402 to continue monitoring for opportunities to intervene in a bad decision by the customer.

Figure 5:
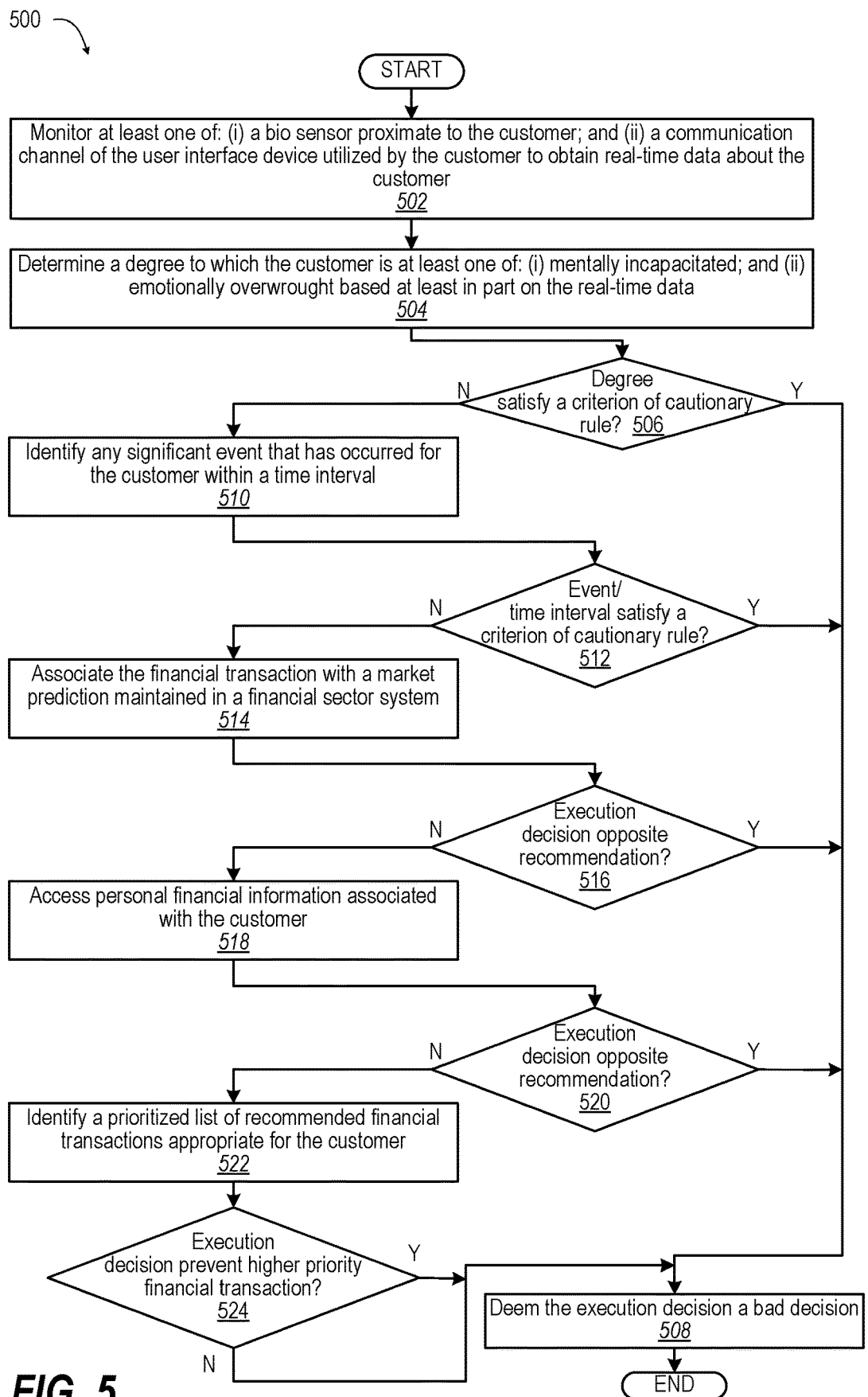
FIG. 5 illustrates a flow diagram of a method of identifying that a cautionary rule is violated by the execution decision of a financial transaction, according to one or more embodiments.

FIG. 5 illustrates a method 500 of identifying that a cautionary rule is violated by the execution decision of a financial transaction. In one or more embodiments, method 500 includes monitoring at least one of: (i) a bio sensor proximate to the customer; and (ii) a communication channel of the user interface device utilized by the customer to obtain real-time data about the customer (block 502). Method 500 includes determining a degree to which the customer is at least one of: (i) mentally incapacitated; and (ii) emotionally overwrought based at least in part on the real-time data (block 504). A determination is made whether the degree satisfies a criterion of the cautionary rule for inability to make a good decision (decision block 506). In response to determining that the degree satisfies the criterion, the execution decision is deemed a bad decision (block 508). Then method 500 ends.

In response to determining that the degree does not satisfy the criterion, method 500 includes identifying any significant event that has occurred for the customer within a time interval (block 510). For example, the event can be a death of a close relative, termination from a job, travel to a foreign country that is associated with a high level of financial fraud, etc. A determination is made as to whether the event and the time interval satisfy a cautionary rule (decision block 512). In response to determining that the degree satisfies the criterion, the execution decision is deemed a bad decision (block 508). Then method 500 ends.

In response to determining that the degree does not satisfy the criterion in decision block 512, method 500 includes associating the financial transaction with a market prediction maintained in a financial sector system (bock 514). A determination is made as to whether the execution decision is opposite to a recommendation based on the market prediction (decision block 516). In response to determining that the execution decision is opposite to a recommendation, the execution decision is deemed a bad decision (block 508). Then method 500 ends.

In response to determining that the execution decision is not opposite to a recommendation in decision block 516, method 500 includes accessing personal financial information associated with the customer (block 518). A determination is made whether the execution decision is opposite to a recommendation derived from the cautionary rule based on the personal financial information (decision block 520). In response to determining that the execution decision is opposite to a recommendation, the execution decision is deemed a bad decision (block 508). Then method 500 ends.

In response to determining that the execution decision is not opposite to a recommendation in decision block 518, method 500 includes identifying a prioritized list of recommended financial transactions appropriate for the customer (block 522). A determination is made based on the personal financial information whether the execution decision prevents execution of a recommended financial transaction that is higher priority (decision block 524). In response to determining that the execution decision prevents a higher priority financial transaction, the execution decision is deemed a bad decision (block 508). Then method 500 ends. In response to determining that the execution decision does not prevent a higher priority financial transaction, method 500 ends.

Figure 6:
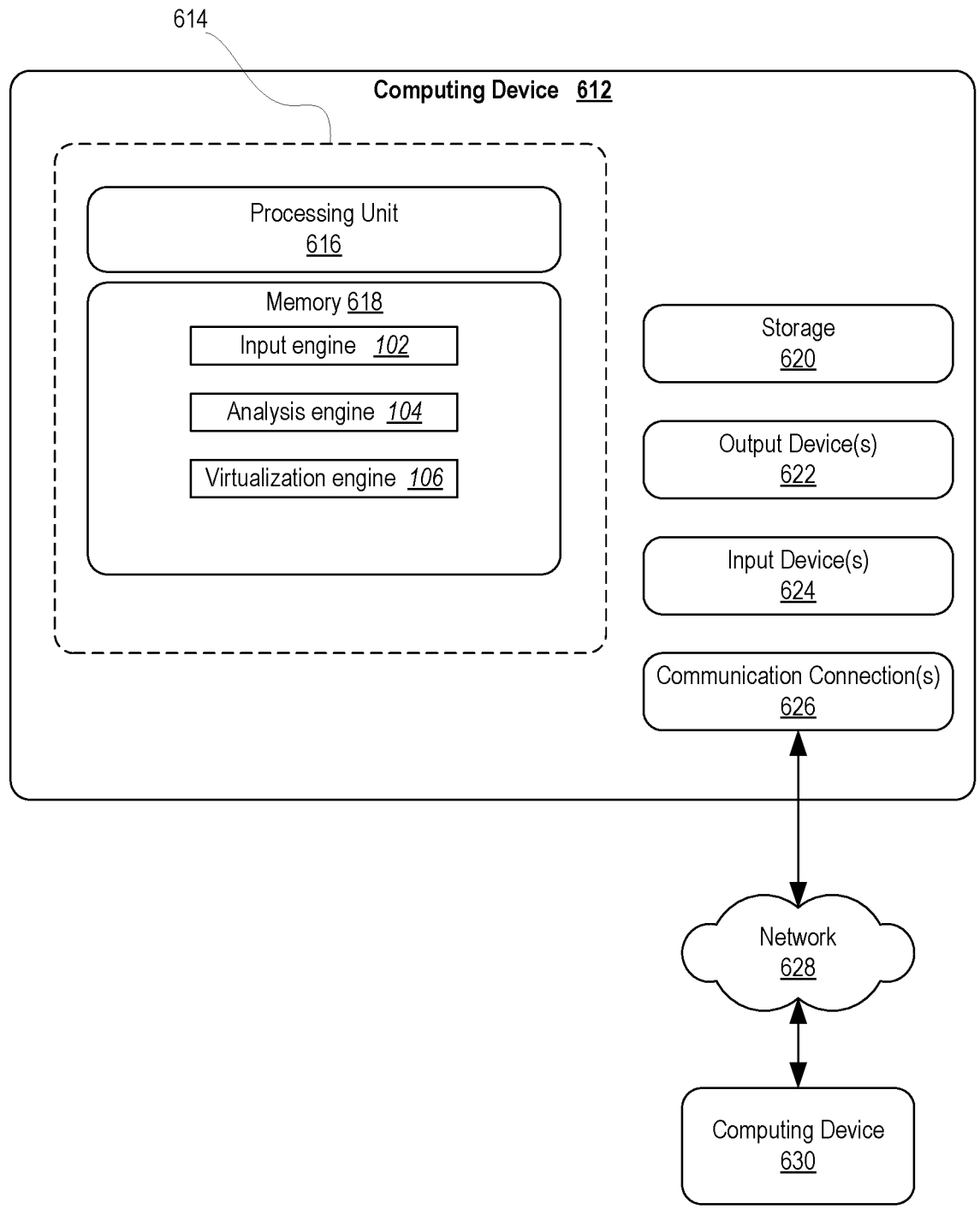
FIG. 6 illustrates a block diagram of a system having a computing device that intervenes in a financial transaction to discourage a bad decision, according to one or more embodiments.

FIG. 6 and the following discussion provide a description of a suitable computing environment to implement embodiments of one or more of the provisions set forth herein. The operating environment of FIG. 6 is merely one example of a suitable operating environment and is not intended to suggest any limitation as to the scope of use or functionality of the operating environment. Example computing devices include, but are not limited to, personal computers, server computers, hand-held or laptop devices, mobile devices, such as mobile phones, Personal Digital Assistants (PDAs), media players, and the like, multiprocessor systems, consumer electronics, mini computers, mainframe computers, distributed computing environments that include any of the above systems or devices, etc.

Generally, embodiments are described in the general context of "computer readable instructions" being executed by one or more computing devices. Computer readable instructions may be distributed via computer readable media as will be discussed below. Computer readable instructions may be implemented as program modules, such as functions, objects, Application Programming Interfaces (APIs), data structures, and the like, that perform one or more tasks or implement one or more abstract data types. Typically, the functionality of the computer readable instructions are combined or distributed as desired in various environments.

FIG. 6 illustrates a system 600 including a computing device 612 configured to implement one or more embodiments provided herein. In one configuration, computing device 612 includes at least one processing unit 316 and memory 618. Depending on the exact configuration and type of computing device, memory 618 may be volatile, such as RAM, non-volatile, such as ROM, flash memory, etc., or a combination of the two. This configuration is illustrated in FIG. 6 by dashed line 614.

In other embodiments, device 612 includes additional features or functionality. For example, device 612 may include additional storage such as removable storage or non-removable storage, including, but not limited to, magnetic storage, optical storage, etc. Such additional storage is illustrated in FIG. 6 by storage 620. In one or more embodiments, computer readable instructions to implement one or more embodiments provided herein are in storage 620. Storage 620 may store other computer readable instructions to implement an operating system, an application program, etc. Computer readable instructions may be loaded in memory 618 for execution by processing unit 616, for example.

The term "computer readable media" as used herein includes computer storage media. Computer storage media includes volatile and nonvolatile, removable and non-removable media implemented in any method or technology for storage of information such as computer readable instructions or other data. Memory 618 and storage 620 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which may be used to store the desired information and which may be accessed by device 612. Any such computer storage media is part of device 612.

The term "computer readable media" includes communication media. Communication media typically embodies computer readable instructions or other data in a "modulated data signal" such as a carrier wave or other transport mechanism and includes any information delivery media.

The term "modulated data signal" includes a signal that has one or more of its characteristics set or changed in such a manner as to encode information in the signal.

Device 612 includes input device(s) 624 such as keyboard, mouse, pen, voice input device, touch input device, infrared cameras, video input devices, or any other input device. Output device(s) 622 such as one or more displays, speakers, printers, or any other output device may be included with device 612. Input device(s) 624 and output device(s) 622 may be connected to device 612 via a wired connection, wireless connection, or any combination thereof. In one or more embodiments, an input device or an output device from another computing device may be used as input device(s) 624 or output device(s) 622 for computing device 612. Device 612 may include communication connection(s) 626 to facilitate communications via a network 628 with one or more other computing devices 630.

Certain functionalities can be performed by software applications resident in memory 618, such as input engine 102, analysis engine 104, and virtualization engine 104.

Figure 7:
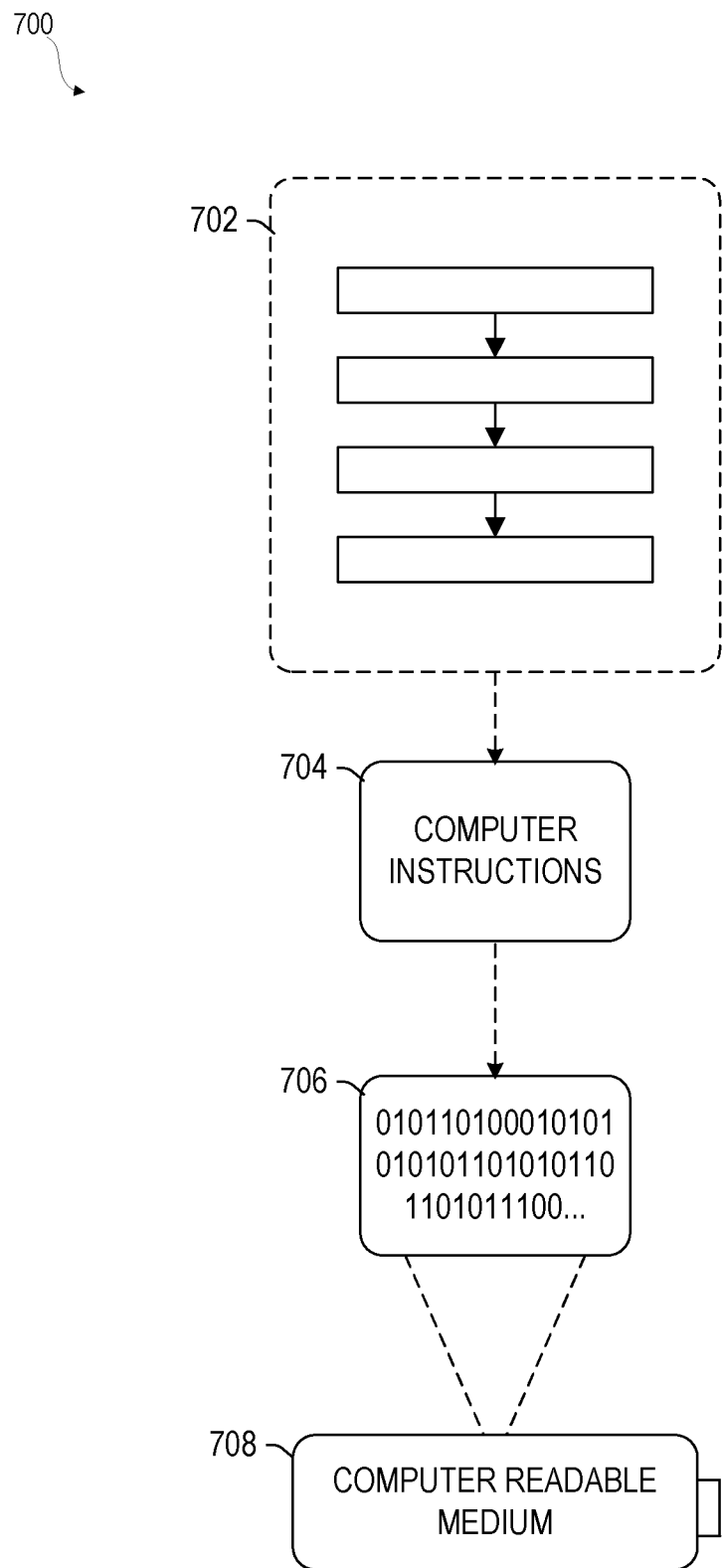
FIG. 7 illustrates a block diagram of example computer-readable medium or computer-readable device including processor-executable instructions configured to embody one or more of the provisions set forth herein, according to one or more embodiments.

Still another embodiment involves a computer-readable medium including processor-executable instructions configured to implement one or more embodiments of the techniques presented herein. An embodiment of a computer-readable medium or a computer-readable device devised in these ways is illustrated in FIG. 7, wherein an implementation 700 includes a computer-readable medium 708, such as a CD-R, DVD-R, flash drive, a platter of a hard disk drive, etc., on which is encoded computer-readable data 706. This computer-readable data 706, such as binary data including a plurality of zero's and one's as shown in 706, in turn includes a set of computer instructions 704 configured to operate according to one or more of the principles set forth herein. In one such embodiment 700, the processor-executable computer instructions 704 may be configured to perform a method, such as method 300 of FIG. 3, method 400 of FIG. 4, or method 500 of FIG. 5. In another embodiment, the processor-executable instructions 704 may be configured to implement a system, such as the system 100 of FIG. 1 or system 200 of FIG. 2. Many such computer-readable media may be devised by those of ordinary skill in the art that are configured to operate in accordance with the techniques presented herein.

One or more embodiments may employ various artificial intelligence (AI) based schemes for carrying out various aspects thereof. One or more aspects may be facilitated via an automatic classifier system or process. A classifier is a function that maps an input attribute vector, x=(x1, x2, x3, x4, xn), to a confidence that the input belongs to a class. In other words, f(x)=confidence (class). Such classification may employ a probabilistic or statistical-based analysis (e.g., factoring into the analysis utilities and costs) to prognose or infer an action that a user desires to be automatically performed.

A support vector machine (SVM) is an example of a classifier that may be employed. The SVM operates by finding a hypersurface in the space of possible inputs, which the hypersurface attempts to split the triggering criteria from the non-triggering events. Intuitively, this makes the classification correct for testing data that may be similar, but not necessarily identical to training data. Other directed and undirected model classification approaches (e.g., naïve Bayes, Bayesian networks, decision trees, neural networks, fuzzy logic models, and probabilistic classification models) providing different patterns of independence may be employed. Classification as used herein, may be inclusive of statistical regression utilized to develop models of priority.

One or more embodiments may employ classifiers that are explicitly trained (e.g., via a generic training data) as well as classifiers which are implicitly trained (e.g., via observing user behavior, receiving extrinsic information). For example, SVMs may be configured via a learning or training phase within a classifier constructor and feature selection module. Thus, a classifier may be used to automatically learn and perform a number of functions, including but not limited to determining according to a predetermined criteria.

As used in this application, the terms "component", "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, or a computer. By way of illustration, both an application running on a controller and the controller may be a component. One or more components residing within a process or thread of execution and a component may be localized on one computer or distributed between two or more computers.

Further, the claimed subject matter is implemented as a method, apparatus, or article of manufacture using standard programming or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Although the subject matter has been described in language specific to structural features or methodological acts, it is to be understood that the subject matter of the appended claims is not necessarily limited to the specific features or acts described above. Rather, the specific features and acts described above are disclosed as example embodiments.

Various operations of embodiments are provided herein. The order in which one or more or all of the operations are described should not be construed as to imply that these operations are necessarily order dependent. Alternative ordering will be appreciated based on this description. Further, not all operations may necessarily be present in each embodiment provided herein.

As used in this application, "or" is intended to mean an inclusive "or" rather than an exclusive "or". Further, an inclusive "or" may include any combination thereof (e.g., A, B, or any combination thereof). In addition, "a" and "an" as used in this application are generally construed to mean "one or more" unless specified otherwise or clear from context to be directed to a singular form. Additionally, at least one of A and B and/or the like generally means A or B or both A and B. Further, to the extent that "includes", "having", "has", "with", or variants thereof are used in either the detailed description or the claims, such terms are intended to be inclusive in a manner similar to the term "comprising".

Further, unless specified otherwise, "first", "second", or the like are not intended to imply a temporal aspect, a spatial aspect, an ordering, etc. Rather, such terms are merely used as identifiers, names, etc. for features, elements, items, etc. For example, a first channel and a second channel generally correspond to channel A and channel B or two different or two identical channels or the same channel. Additionally, "comprising", "comprises", "including", "includes", or the like generally means comprising or including, but not limited to.

Although the disclosure has been shown and described with respect to one or more implementations, equivalent alterations and modifications will occur based on a reading and understanding of this specification and the annexed drawings. The disclosure includes all such modifications and alterations and is limited only by the scope of the following claims.

What is claimed is:

1. A method of intervening in a financial transaction to discourage a bad decision by a customer, the method comprising:
    analyzing an execution decision by a customer for a financial transaction;
    identifying a cautionary rule that is violated by the execution decision, the identifying comprising:
        identifying an event that has occurred for the customer within a time interval, wherein the event is a life event associated with inducing an abnormal state of mind of the customer, and
        associating the event and the time interval with the cautionary rule;
    monitoring the customer during communication with one or more persons;
    detecting a positive response to a selected person of the one or more persons that indicates a persuasive relationship with the customer, wherein detecting the positive response to the selected person of the one or more persons that indicates the persuasive relationship with the customer comprises:
        determining that the selected person is communicating with the customer,
        detecting a positive physiological response by the customer to the communication, wherein the positive physiological response is not a conscious physical act performed by the customer,
        determining that the positive physiological response correlates to a first persuasive relationship,
        characterizing the selected person as having a persuasive relationship with the customer in a first type of financial transaction,
        detecting a second positive physiological response by the customer to a second person, and
        characterizing the second person as having a second persuasive relationship with the customer in a second type of financial transaction;
    capturing, using an audio and video capture, a persona of the selected person for communicating with the customer via a user interface device; and
    presenting, on at least one user interface device to the customer, a suggestion in a personally persuasive persona, wherein presenting the suggestion in the personally persuasive persona comprises:
        rendering an image of the persona of the selected person into a three-dimensional holographic image such that the three-dimensional holographic image mimics body language, gestures, and appearance of the selected person,
        modulating voice qualities of text-to-voice playback to mimic speech by the selected person, and
        presenting the suggestion in the personally persuasive persona of the selected person in response to determining that the financial transaction is the first type of financial transaction.

2. The method of claim 1, wherein detecting the positive response to the selected person of the one or more persons that indicates the persuasive relationship with the customer comprises associating a good decision occurring after a corresponding suggestion by the selected person to the customer.

3. The method of claim 1, wherein identifying the cautionary rule that is violated by the execution decision further comprises:
    monitoring at least one of: (i) a bio sensor proximate to the customer and (ii) a communication channel of the user interface device utilized by the customer to obtain real-time data about the customer;
    determining a degree to which the customer is at least one of: (i) mentally incapacitated and (ii) emotionally overwrought based at least in part on the real-time data; and
    determining that the degree satisfies a criterion of the cautionary rule for inability to make a good decision.

4. The method of claim 1, wherein identifying the cautionary rule that is violated by the execution decision further comprises:
    associating the financial transaction with a market prediction maintained in a financial sector system; and
    determining that the execution decision is opposite to a recommendation based on the market prediction.

5. The method of claim 1, wherein identifying the cautionary rule that is violated by the execution decision further comprises:
    accessing personal financial information associated with the customer; and
    determining that the execution decision is opposite to a recommendation derived from the cautionary rule based on the personal financial information.

6. The method of claim 1, further comprising:
    identifying a prioritized list of recommended financial transactions appropriate for the customer,
    wherein identifying the cautionary rule that is violated by the execution decision further comprises determining, based on personal financial information, that the execution decision prevents execution of a recommended financial transaction that is higher priority.

7. The method of claim 1, wherein the modulating the voice qualities comprises:
    analyzing biological factors to derive the modulation of the voice qualities.

8. The method of claim 7, comprising:
    collecting biological factors of the customer and people m close network of the customer, wherein the biological factors include voice, images, text messages, body language, gestures and thought process.

9. A system comprising:
    an input engine that monitors at least one user interface device of a customer;
    an analysis engine that:
        (i) analyzes an execution decision by the customer made on the at least one user interface device for a financial transaction,
        (ii) identifies a cautionary rule that is violated by the execution decision, and
        (iii) identifies that the execution decision by the customer is made at an inappropriate time, the identification comprising:
            identifying an event that has occurred for the customer within a time interval, wherein the event is a life event associated with inducing an abnormal state of mind of the customer; and associating the event and the time interval with the cautionary rule;

a virtualization engine that presents on at least one user interface device to the customer a suggestion in a personally persuasive persona, wherein:

the input engine: (i) monitors the at least one user interface device of the customer during communication with one or more persons and (ii) detects a response to a selected person of the one or more persons;

the analysis engine: determines that the response is a positive physiological response to the selected person of the one or more persons that indicates a persuasive relationship with the customer by: (i) associating a good decision occurring after a corresponding suggestion by the selected person to the customer; and (ii) detecting the positive physiological response by:

determining that the selected person is communicating with the customer, detecting the positive physiological response by the customer to the communication, wherein the positive physiological response is not a conscious physical act performed by the customer, and determining that the positive physiological response correlates to the persuasive relationship, wherein:

the analysis engine: (i) determines the positive physiological response by the customer to a second person, (ii) characterizes the selected person as having the persuasive relationship with the customer in a first type of financial transaction, (iii) characterizes the second person as having a second persuasive relationship with the customer in a second type of financial transaction, and (iv) determines that the financial transaction is the first type;

and the virtualization engine:

captures, using an audio and video capture, a persona of the selected person for communicating with the customer via the at least one user interface device, and presents on the at least one user interface device to the customer a suggestion in a personally persuasive persona, wherein presenting the suggestion in the personally persuasive persona comprises:

rendering an image of the persona of the selected person into a three-dimensional holographic image such that the three-dimensional holographic image mimics body language, gestures, and appearance of the selected person on the at least one user interface device;

modulating voice qualities of text-to-voice playback to mimic speech by the selected person on the at least one user interface device; and presents the suggestion in the personally persuasive persona of the selected person in response to the analysis engine determining that the financial transaction is the first type of financial transaction.

10. The system of claim 9, wherein:

the input engine monitors at least one of: (i) a bio sensor proximate to the customer; and (ii) a communication channel of the at least one user interface device utilized by the customer to obtain real-time data about the customer;

the analysis engine determines a degree to which the customer is at least one of: (i) mentally incapacitated; and (ii) emotionally overwrought based at least in part on the real-time data; and the analysis engine identifies the cautionary rule that is violated by the execution decision by determining that the degree satisfies a criterion of the cautionary rule for inability to make a good decision.

11. The system of claim 9, wherein the analysis engine identifies the cautionary rule that is violated by the execution decision by:

identifying that the execution decision by the customer is objectively a bad decision, the identification comprising:

associating the financial transaction with a market prediction maintained in a financial sector system, and determining that the execution decision is opposite to a recommendation based on the market prediction; and identifying that the execution decision by the customer is subjectively a bad decision, the identification comprising:

accessing personal financial information associated with the customer; and determining that the execution decision is opposite to a recommendation derived from the cautionary rule based on the personal financial information.

12. The system of claim 11, wherein the analysis engine:

identifies a prioritized list of recommended financial transactions appropriate for the customer; and identifies the cautionary rule that is violated by the execution decision by determining, based on the personal financial information, that the execution decision prevents execution of a recommended financial transaction that is higher priority.

13. The method of claim 9, comprising:

collecting biological factors of the customer and people m close network of the customer, wherein the biological factors include voice, images, text messages, body language, gestures and thought process; and analyzing the biological factors to derive the modulation of the voice qualities.

14. A non-transitory computer-readable storage medium comprising computer-executable instructions, which when executed via a processing unit on a computer performs acts, comprising:

analyzing an execution decision by a customer for a financial transaction;

identifying a cautionary rule that is violated by the execution decision, the identifying comprising:

identifying an event that has occurred for the customer within a time interval, wherein the event is a life event associated with inducing an abnormal state of mind of the customer, and associating the event and the time interval with the cautionary rule;

monitoring the customer during communication with one or more persons;

detecting a positive response to a selected person of the one or more persons that indicates a persuasive relationship with the customer, wherein detecting the positive response to a selected person of the one or more persons that indicates the persuasive relationship with the customer comprises:

determining that the selected person is communicating with the customer, detecting a positive physiological response by the customer to the communication, wherein the positive physiological response is not a conscious physical act performed by the customer, determining that the positive physiological response correlates to a first persuasive relationship, characterizing the selected person as having a persuasive relationship with the customer in a first type of financial transaction, detecting a second positive physiological response by the customer to a second person, and characterizing the second person as having a second persuasive relationship with the customer in a second type of financial transaction;

capturing, using an audio and video capture, a persona of the selected person for communicating with the customer via the user interface device; and presenting on the user interface device to the customer a suggestion in a personally persuasive persona, wherein presenting the suggestion in the personally persuasive persona comprises:

rendering an image of the persona of the selected person into a three-dimensional holographic image such that the three-dimensional holographic image mimics body language, gestures, and appearance of the selected person, modulating voice qualities of text-to-voice playback to mimic speech by the selected person, and presenting the suggestion in the personally persuasive persona of the selected person in response to determining that the financial transaction is the first type of financial transaction.

15. The non-transitory computer-readable storage medium of claim 14, wherein the modulation comprises:
analyzing biological factors to derive the modulation of the voice qualities.

16. The non-transitory computer-readable storage medium of claim 15, comprising:
collecting the biological factors of the customer and people in close network of the customer, wherein the biological factors include voice, images, text messages, body language, gestures and thought process.

* * * * *

UNITED STATES PATENT AND TRADEMARK OFFICE
CERTIFICATE OF CORRECTION

PATENT NO. : 11,238,518 B2
APPLICATION NO. : 15/842238
DATED : February 1, 2022
INVENTOR(S) : Ravi Kumar Gokanakonda et al.

It is certified that error appears in the above-identified patent and that said Letters Patent is hereby corrected as shown below:

In the Claims

Claim 8, Column 2, Lines 48-49 reading -collecting biological factors of the customer and people m close network of the customer, wherein the biological- should read --collecting the biological factors of the customer and people in close network of the customer, wherein the biological--

Signed and Sealed this
Twentieth Day of December, 2022

Katherine Kelly Vidal
*Director of the United States Patent and Trademark Office*